(12) United States Patent
Brand-Meier et al.

(10) Patent No.: US 9,638,612 B2
(45) Date of Patent: May 2, 2017

(54) SELECTIVE RELEASE OF SUB-GROUP OF BIOLOGICAL UNITS

(71) Applicant: Roche Molecular Systems, Inc., Pleasanton, CA (US)

(72) Inventors: Judith Brand-Meier, Hedingen (CH); Claudio Cherubini, Cham (CH); Andreas Drechsler, Baar (CH); Nicole Gwerder, Buchrain (CH); Martin Kopp, Huenenberg See (CH); Edwin Oosterbroek, Cham (CH); Emad Sarofim, Hagendorn (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 4 days.

(21) Appl. No.: 14/261,678

(22) Filed: Apr. 25, 2014

(65) Prior Publication Data
US 2014/0329249 A1    Nov. 6, 2014

(30) Foreign Application Priority Data
May 1, 2013    (EP) .................................. 13166110

(51) Int. Cl.
*C40B 80/00* (2006.01)
*C40B 40/02* (2006.01)
*G01N 1/44* (2006.01)
*G01N 33/567* (2006.01)
*G01N 33/574* (2006.01)
*G01N 33/543* (2006.01)

(52) U.S. Cl.
CPC ......... *G01N 1/44* (2013.01); *G01N 33/54353* (2013.01)

(58) Field of Classification Search
CPC .......... C12C 1/68; C07H 21/02; G01N 31/22; G01N 33/53; G01N 33/54353; G01N 33/567; G01N 33/574; C40B 80/00; C40B 30/04
USPC ......... 506/14, 142; 435/6.1, 7.21, 7.23, 7.24
See application file for complete search history.

(56) References Cited

U.S. PATENT DOCUMENTS

| | | | |
|---|---|---|---|
| 5,998,129 A | 12/1999 | Schutze et al. | |
| 6,057,096 A * | 5/2000 | Rothschild | C07H 19/04 |
| | | | 435/6.13 |
| 6,087,134 A | 7/2000 | Saunders | |
| 6,093,370 A * | 7/2000 | Yasuda | B01L 3/5027 |
| | | | 422/504 |
| 6,358,749 B1 | 3/2002 | Orthman | |
| 6,531,278 B1 | 3/2003 | Weimer | |
| 2007/0238122 A1 | 10/2007 | Allbritton et al. | |
| 2010/0294952 A1 * | 11/2010 | Mirkin et al. | 250/492.1 |
| 2011/0079552 A1 | 4/2011 | Yagi | |
| 2011/0124037 A1 | 5/2011 | Backhaus et al. | |
| 2014/0134646 A1 * | 5/2014 | Martin | G01N 33/56966 |
| | | | 435/7.23 |

FOREIGN PATENT DOCUMENTS

| | | |
|---|---|---|
| EP | 0539888 A1 | 5/1993 |
| EP | 1367380 A1 | 12/2003 |
| EP | 2083257 A1 | 7/2009 |
| WO | 9627132 A1 | 9/1996 |
| WO | 2009076560 A2 | 6/2009 |
| WO | 2009076560 A3 | 6/2009 |

OTHER PUBLICATIONS

Shin et al, Photolabile micropatterned surfaces for cell capture and release, 2011, Chem. Commun., 47, 11942-11944.*
Probst et al, Rapid Multitarget Immunomagnetic Separation through Programmable DNA Linker Displacement, 2011, JACS, 133, 17126-17129.*
Parker et al, Photocleavable peptide hydrogel arrays for MALDI-TOF analysis of kinase activity, 2006, Ananlyst, 131, 1097-1104.*
Wirkner et al, Triggered Cell Release from Material Using Bioadhesive Photocleavable Linkers, 2001, Adv. Mater., 23, 3907-3910.*
Wijaya, Andy, et al., "Selective release of multiple DNA Oligonucleotides from Gold Nanorods", ACS Nano, vol. 3, No. 1, Jan. 27, 2009, p. 80-86.
Wang, Rong, et al., "Traceless Cross-Linker for Photocleavable Bioconjugation", Bioconjugate Chem., vol. 23, Apr. 13, 2012, p. 705-713.
Bombera, Radoslaw, et al., "DNA-directed capture of primary cells from a complex mixture and controlled orthogonal release monitored by SPR imaging", Biosensors and Bioelectronics, vol. 33, No. 1, Mar. 1, 2012, p. 10-16.

* cited by examiner

*Primary Examiner* — Narayan Bhat
(74) *Attorney, Agent, or Firm* — Pamela C. Ancona; M. Reza Savari

(57) ABSTRACT

A method of individually releasing from an entity one or more members of a sub-group of biological units included in a heterogeneous group of biological units is provided. The method includes binding the group of biological units including the sub-group of biological units to the entity via a linker. Following binding, the location of the one or more members on the entity is determined. Once the location is determined, a localized physical pulse is applied to the one or more members. The localized physical pulse individually releases the one or more members from the entity by dissociating the linker.

13 Claims, 11 Drawing Sheets

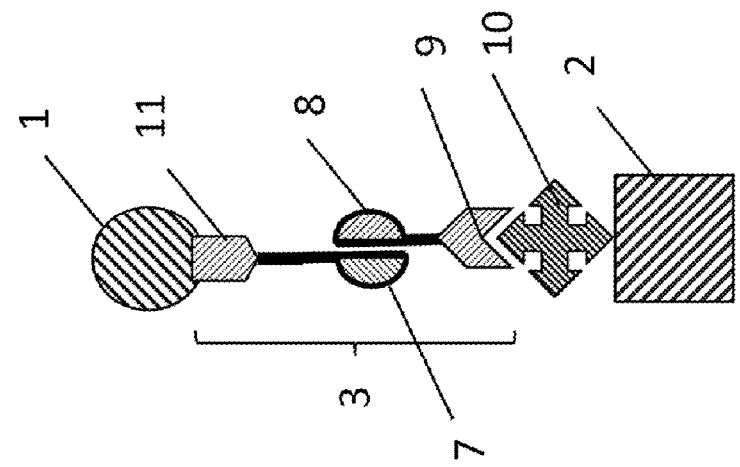
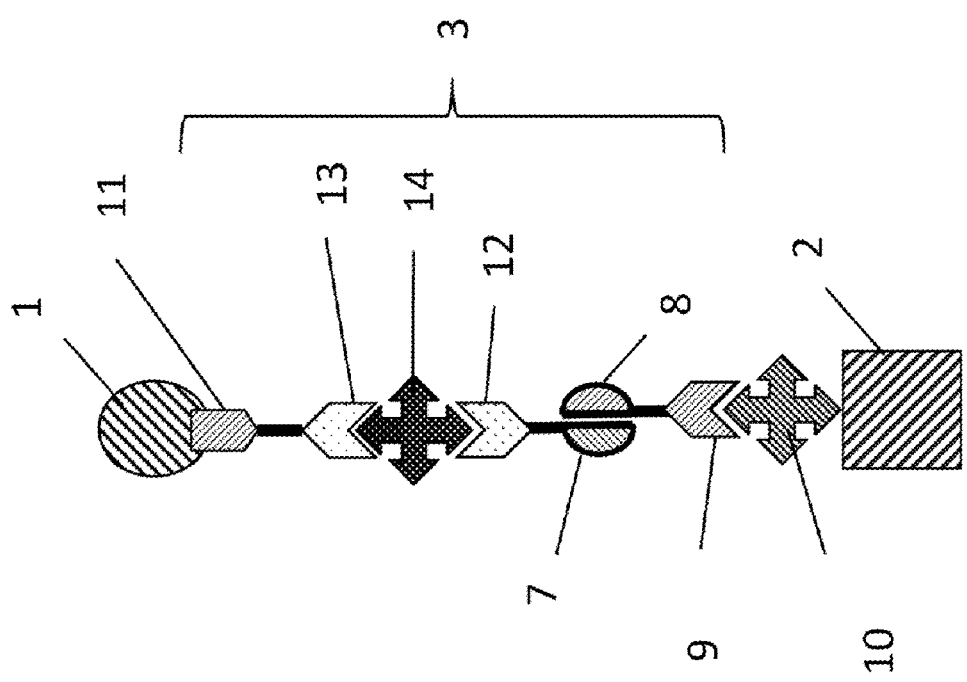

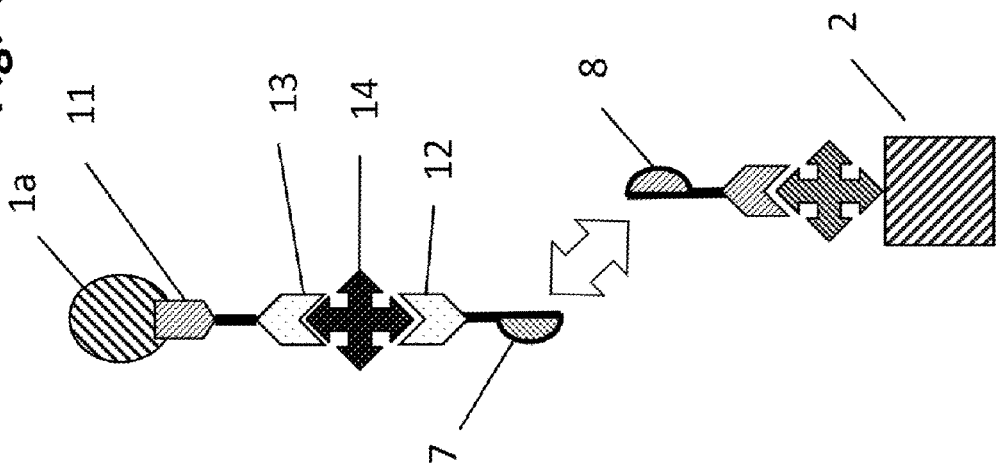
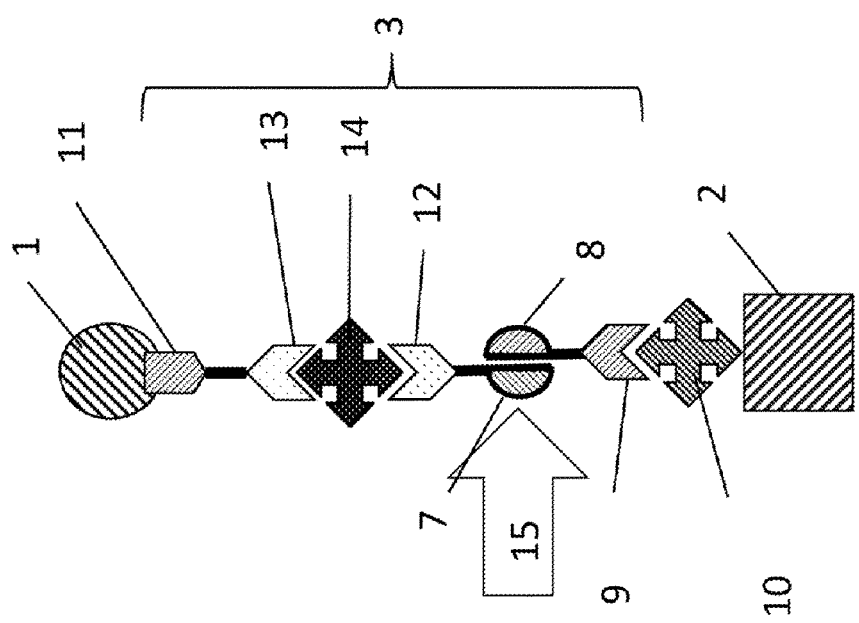

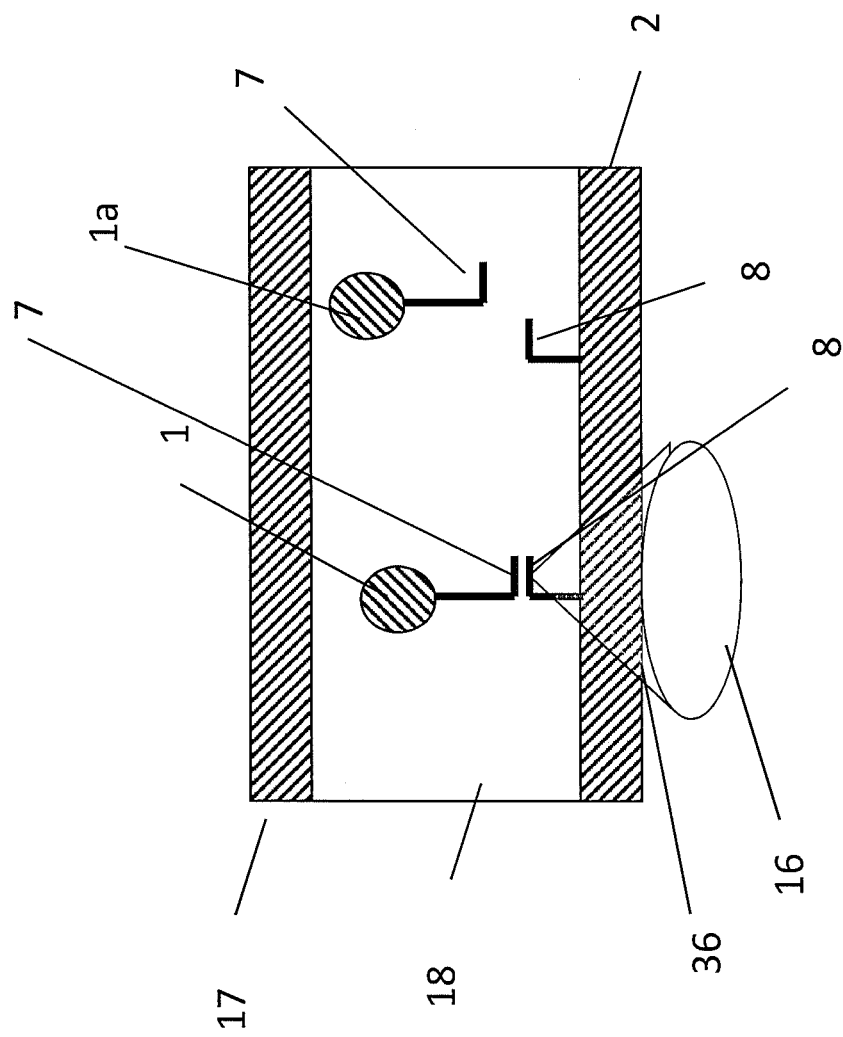

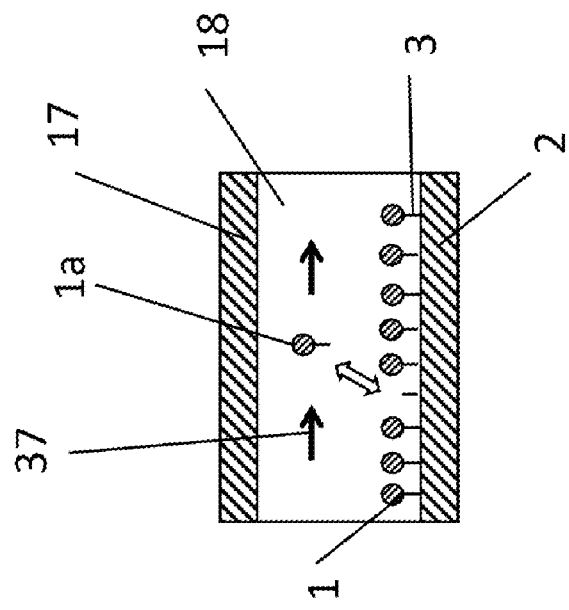
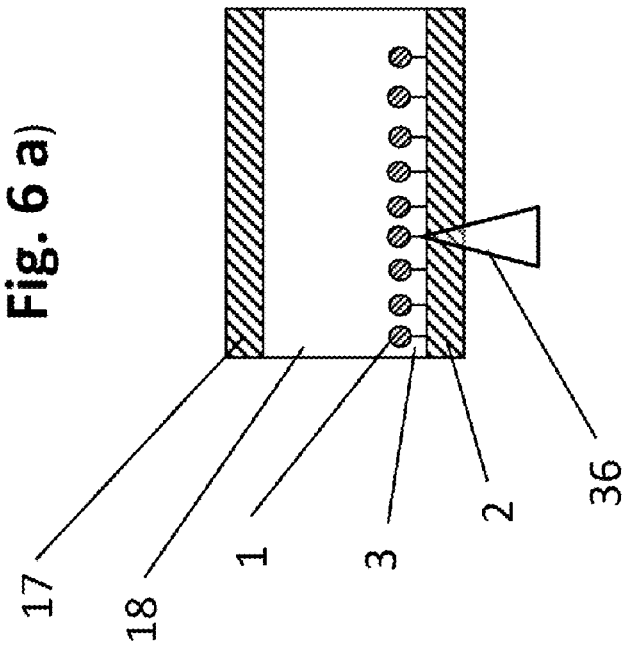
Fig. 6 a)
Fig. 6 b)

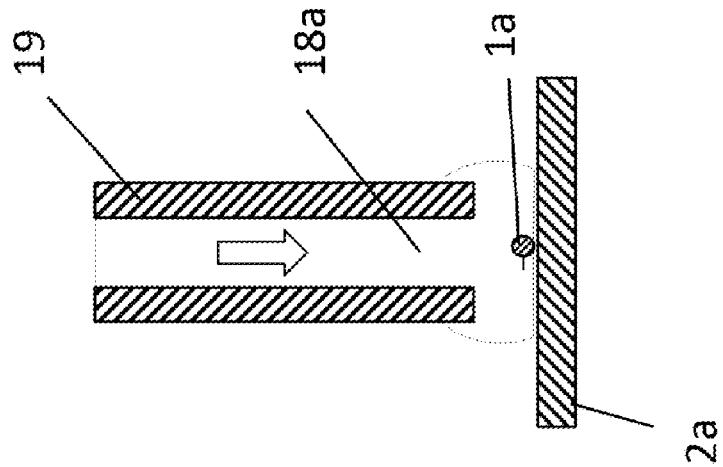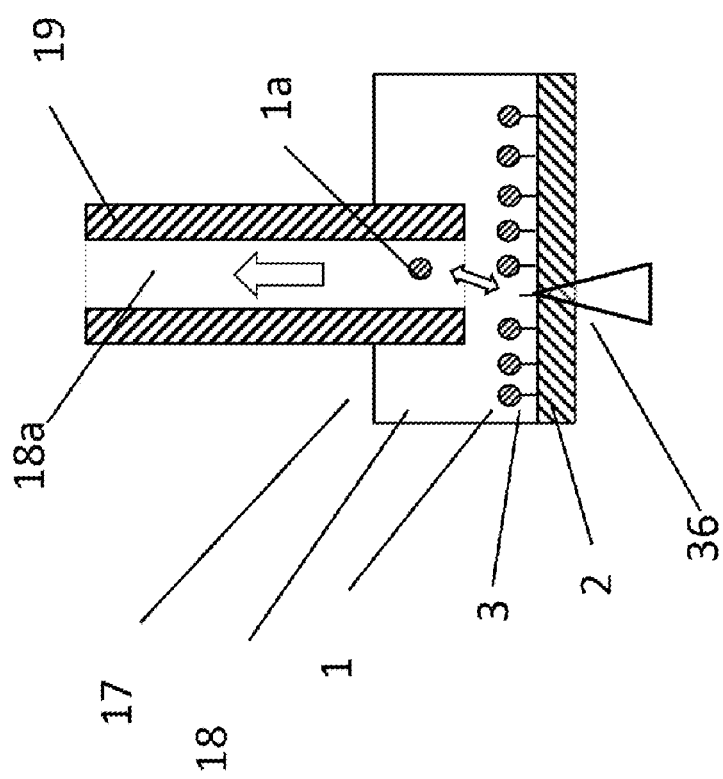

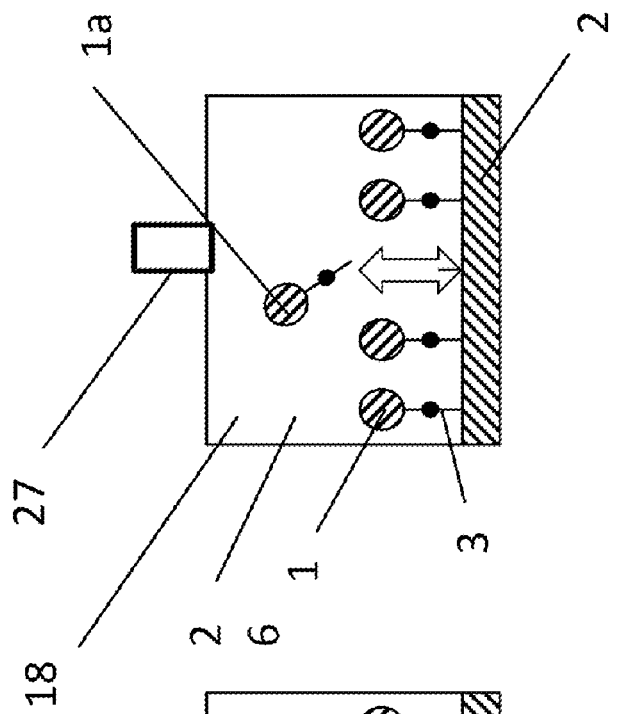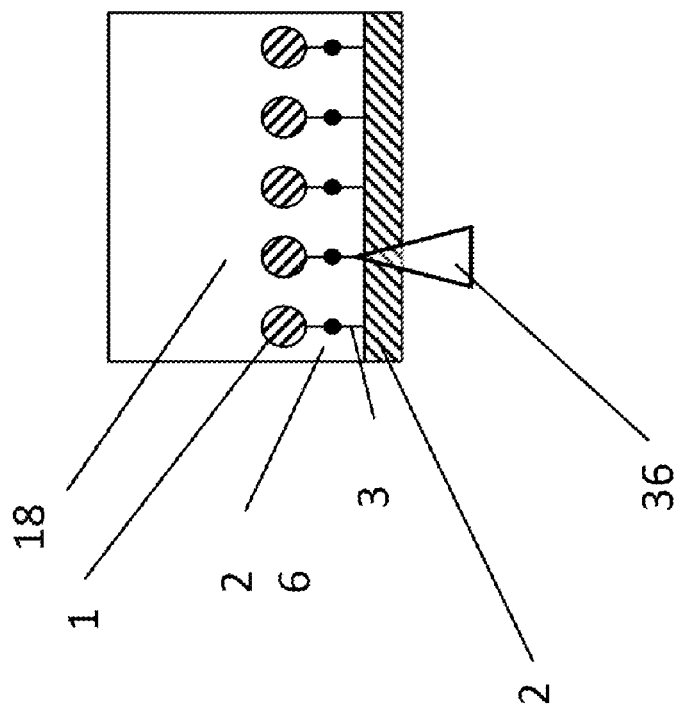

SELECTIVE RELEASE OF SUB-GROUP OF BIOLOGICAL UNITS

CROSS-REFERENCES TO RELATED APPLICATIONS

The present application claims the benefit of priority under 35 U.S.C. §119 of EP13166110.0, filed May 1, 2013, the content of which is incorporated by reference herein in its entirety.

FIELD OF THE INVENTION

The present disclosure relates to a method of individually releasing from an entity one or more members of a sub-group of biological units comprised in a heterogeneous group of biological units, a method of detecting a subject's disease by detecting a sub-group of biological units obtained from said subject, and a method of isolating one or more members of a sub-group of biological units from a group of biological units.

BACKGROUND OF THE INVENTION

Modern techniques for the analysis of cell biology have created an increasing need to prepare samples composed of a homogeneous population of cells or the detection or isolation of single cells or small particles. Genomic and proteomic studies, genetic cloning, stem cell studies, and cell-based screening would all benefit from an enhanced ability to obtain single cells or small homogeneous biological samples for subsequent analysis. These samples include various molecules such as DNA or RNA as well as cells or organisms.

In the case of selecting cells from a mixed population, individual cells possessing a desired characteristic must be analyzed followed by identification and isolation of a desired subpopulation. Standard sorting methods for mammalian cells require cells to be dispersed in a single-cell suspension, and are most successful with hematopoietic cells which grow naturally in this manner. These methods are less applicable to adherent cells, by far the most common cell phenotype.

Adherent cells are typically analyzed by plating them on a growth surface then looking for them using a microscope. Traditional sorting techniques for separating cells of interest from a mixed population of cells typically require enzymatic or mechanical release of adherent cells from their growth surface which is detrimental to cell health, or involve extended protocols for selection based on limiting dilution or genetically engineered resistance to a selective environment.

Efficient methods to isolate single cells or particles or low numbers thereof of a heterogeneous population which provide undamaged cells or particles suitable for downstream analysis are still missing.

SUMMARY OF THE INVENTION

The present disclosure provides new methods for isolating single cells or particles suitable for downstream analysis and diagnostics.

A method of individually releasing from an entity one or more members of a sub-group of biological units comprised in a heterogeneous group of biological units is provided. The method comprises binding said group of biological units comprising said sub-group of biological units to said entity via a linker. Following binding, the location of said one or more members on said entity is determined. Once the location is determined, a localized physical pulse is applied to said one or more members. The localized physical pulse individually releases the one or more members from the entity by dissociating the linker.

A method of detecting a subject's disease by detecting a sub-group of biological units obtained from said subject, wherein said sub-group of biological units is indicative of the disease is, furthermore, provided. The method comprises providing a heterogeneous group of biological units comprising at least one sub-group of biological units, the group of biological units being obtained from a subject, and each member of the group of biological units being bound to an entity, preferably a solid support via a linker. The location of the sub-group of biological units on the entity is determined. Then, a localized physical pulse is applied to said one or more members. The localized physical pulse individually releases the one or more members from the entity by dissociating the linker. The one or more members of the sub-group of biological units is/are then harvested. By harvesting the one or more members of the sub-group of biological units, the one or more members of the sub-group of biological units is/are isolated. The harvested one or more members is/are then analyzed for the presence of at least one marker indicative of the disease.

A method of isolating one or more members of a subgroup of biological units from a group of biological units, is disclosed. The method comprises Providing a heterogeneous group of biological units comprising at least one sub-group of biological units, each member of the group of the biological units being bound to an entity, preferably a solid support, via a linker; and Determining the location of said one or more members of the sub-group of biological units;

Applying a localized physical pulse to said one or more members, wherein said localized physical pulse individually releases said one or more members from said entity by dissociating said linker;

Isolating the released one or more members of the sub-group of biological units.

BRIEF DESCRIPTION OF THE FIGURES

Other and further objects, features and advantages of the embodiments will appear more fully from the following description. The accompanying drawings, together with the general description given above and the detailed description given below, serve to explain the principles of the embodiments.

FIG. 3a) and FIG. 3b) show schematic views of two different embodiments of the linker (3) which is bound to cell (1) and entity (2).

FIG. 4a) shows a schematic view of the same linker (3) of FIG. 3a) bound to cell (1) and entity (2, and FIG. 4b) shows a schematic view of the process of dissociation of part a and part b for the exemplary embodiment shown in FIG. 3a).

FIG. 5 shows a schematic view of part a (7) and part b (8) are dissociated by a light pulse (36) from a light source (16), resulting in detachment of cell (1a).

FIG. 6a) shows a schematic view of a physical pulse (36) exerted onto a cell (1) using a focused light source (16), and FIG. 6b) shows a schematic view of the individual detachment of cells (1) by a physical pulse (36).

FIG. 7a) shows a schematic view of a pipetting instrument (19) used for removing the selectively released or detached cell (1a) following a light pulse (36), and FIG. 7b) shows a schematic view of the aspirated liquid (18a) comprising detached cell (1a) to be dispensed onto a new surface or a receptacle (2a).

FIG. 8a) shows a schematic view of an embodiment in which a magnetic particle (26) is associated with part a (7) and is detached along with detached cell (1a), and FIG. 8b) shows a schematic view of the released or detached cell (1a) which, can then be harvested using a magnet (27).

DETAILED DESCRIPTION OF THE INVENTION

Figure 1:
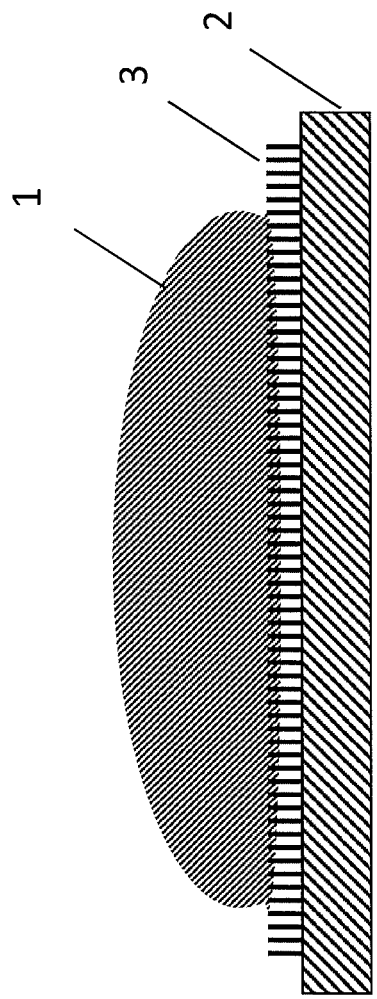
FIG. 1 shows a schematic view of a cell (1) bound to an entity (2) via linkers (3).

By way of illustration, specific exemplary embodiments in which the invention may be practiced now are described.

A method of individually releasing from an entity one or more members of a sub-group of biological units comprised in a heterogeneous group of biological units is described. The method comprises: Binding said group of biological units comprising said sub-group of biological units to said entity via a linker; determining the location of said one or more members on said entity; applying a localized physical pulse to said one or more members, Wherein said localized physical pulse individually releases said one or more members from said entity by dissociating said linker.

The term "individually releasing" means that the one or more members of a sub-group can be released without releasing any other member of another sub-group. In one embodiment, a single member of a subgroup can be individually released without releasing any other member of this sub-group or any other sub-group.

"Entity" refers to an object to which the sub-groups of biological units are bound. In one embodiment, the entity is a binding substrate. In one embodiment, the binding substrate is a solid support. Embodiments of solid supports will be described further below. The term, "member of a sub-group of biological units" relates to an individual part of the subgroup. In an embodiment where the biological units are cells, a member may be a single cell. In an embodiment where the biological units are viral particles, a member may be a single viral particle. In an embodiment in which the biological units are macromolecules, a member may also be a single macromolecule belonging to a sub-group of macromolecules. Besides the embodiments already listed, a biological unit may also be a part of a cell, an organelle, a cellular component, such as a protein nucleic acid, receptor, marker, metabolite etc. A member of any one of said biological units would be derived accordingly.

The term "heterogeneous group of biological units" relates to a group in which not all members are identical. One or more members of a group differ from other members in the group in at least one feature. The one or more members of a sub-group which are identical are referred to as a homogeneous sub-group of objects. For example, the heterogeneous group of biological units may be cells, and the group may comprise different cell types, e.g. cells expressing different surface markers. Such surface markers may, in one embodiment, characterize a specific sub-type of cells, such as a cancer cell.

As described above, a group of biological units comprising a sub-group of biological units is bound to the entity via a linker. The linker is a structure capable of binding the members of the group of biological units and the entity to which the members of the group of biological units are bound. The linker, thus, forms a link between a member and the entity, thus allowing the member to be bound to the entity. Furthermore, the linker is formed such that it can be dissociated into multiple parts when a physical pulse is applied. This, then, makes it possible to release a member from the entity, Specific embodiments of linkers are further described below.

In one embodiment, biological units are immobilized on an entity using centrifugation. Centrifugation is performed at a speed which is sufficient to allow the cells to contact the entity more quickly without causing damage to the cells. In one embodiment, the cells are directly contacted with the entity. In another embodiment, the cells are contacted with a linker which is attached to the entity. The advantage of this method is that the cells can be immobilized more quickly. An exemplary device for carrying out this method is described herein.

In the above method, the location of the one or more members is determined. The determination of the location of the one or more members can be done with any suitable means known to the skilled person. In one embodiment, the determining of the location is performed by observation with a microscope, a scanning microscope or an optical scanner. In one embodiment, the one or more members are made visible with a fluorescent dye which specifically binds to the one or more members of the subgroup of biological units, and an optical fluorescence microscope can be used to localize. In one embodiment, the microscope is an automatic microscope with a camera and scanning or positioning stage using automatic image processing to find the location of the one or more members automatically based on staining of the one or more members or their shape etc. The coordinate list defining the location of the one or more members is then transferred to the control unit for positioning the physical pulse to release the one or more members. In another embodiment, the microscope is a manual microscope. The operator selects the one or more members of the sub-group of biological units. A coordinate list of the selected one or more members of the sub-group of biological units is transferred to a control unit for positioning the physical pulse to release the one or more members.

Once the location of the one or more members of the sub-group of biological units is determined, a localized physical pulse is applied to the one or more members that are to be released. Thus, the localized pulse can be precisely applied. In one embodiment, the localized pulse is applied to a single member of the subgroup of biological units. This has the advantage that each member of the sub-group of biological units can be released and harvested either individually or collectively.

In one embodiment, the physical pulse is selected from photonic light sources, thermal sources and arrangements. Arrangements are combinations of light or thermal sources with other means, e.g. free space optics, fiber optics, mechanic arrangements. Specific embodiments are focused light sources, fiber coupled light sources, arrayed light sources which consist of a matrix with addressable pixels with a light emitting element at each crossing; or an arrayed heat source which consists of a matrix with addressable pixels with resistive heating elements at each crossing.

In one embodiment, the photonic light sources are selected from LASER, LED, Gas discharge lamp, metal vapor lamp, or other kinds of thermal or non-thermal light sources. The LASER's wavelength may be visible or invisible. The light source's wavelength may be in the range of UV, visible light or IR. The LED may be a high power LED. The LED or high power LED may be visible, invisible or UV.

In one embodiment, the thermal sources are selected from infrared LASER, Infrared LED or high power LED or resistive heater.

The arrangements may, in one embodiment, be selected from focused light sources, fiber coupled light sources, arrayed light sources, matrix with addressable pixels for light generation or matrix with addressable pads for heat generation.

The localized physical pulse individually releases the one or more members of the sub-group of biological units which is/are to be released by dissociating the linker and, thus, allowing said members to separate from the entity. Released members can then be harvested.

The method described herein has several advantages. Biological units such as cells can be analyzed, manipulated and treated before releasing them from the entity. The method allows binding to the entity to be non-specific, i.e. all members can be bound independent of the sub-group to which they belong. This makes it possible to sequentially localize, release and harvest members of different sub-groups, i.e. in a first round, one or more members of sub-group 1 characterized by feature 1 are localized, released and harvested. Afterwards, using the same entity with bound biological units, one or more members of sub-group 2 characterized by feature 2 can be localized, released and harvested etc. The remaining cells can also be further manipulated and observed, and after the manipulation or based on a further feature, a new set of members of a sub-group of biological units can be observed, selected, released and harvested.

It is possible with the method described herein to select, release and harvest a single biological unit, such as, in one embodiment, a cell. It is also possible to select, release and harvest multiple cells or a batch of cells.

A particular advantage of the method described herein is that since the physical pulse for dissociation of the linker molecules can be localized, members can be observed with a microscope, a scanning microscope or an optical scanner, individually selected and detached.

The harvesting of a member or members should provide a high purity due to precise localization and resolution, and by the short time of application of the physical pulse.

Harvesting may comprise collection of cells into a collection volume for downstream analysis using, e.g. flow, gravity, optical tweezers, mechanic or magnetic forces, micro pipettors or manipulators. Such devices are known to the person skilled in the art.

With the present method, it is possible to achieve a high packing density of the biological units on the entity due to precise localization of the physical pulse with reduced wasted areas.

As the same linker molecule is used for binding of all of the biological units, a high yield can be obtained independent of the sub-group that members belong to.

One particular advantage of the present method is that a high cell integrity can be obtained due to the gentle methods for releasing the members. No scratching or high forces are applied which could cause damage to the biological units. The physiological environment of the biological units remains unchanged during the processing and harvesting of members. This preserves the integrity of the harvested biological units. A further advantage is that the one or more members of the sub-group of biological units can be harvested much faster than using other mechanical methods, in particular if a large number of cells have to be released.

The one or more member harvested by the method herein described can be directly fed into downstream analysis without need for complex washing procedures or additional handling. There can also be no contamination of ambient liquid which may affect the integrity of the biological units.

In case a thermal pulse is used instead of an optical pulse, an advantage is that there is no interference with optical properties of fluorescent dyes which may be used to localize the one or more members of the biological units to be released and harvested. In addition, there is no interference with binding of the biological units during optical inspection if a thermal pulse is used.

In one embodiment, a combination of an optical pulse and a reagent can be used to release the one or more members of the biological units. This would allow the optical inspection of the members in the absence of the reagent without affecting binding to the entity. The release of the one or more members of a sub-group of biological units would then occur in the presence of the reagent. In one embodiment, the reagent is a photo acid generator.

According to one embodiment, the biological units are bound to the entity via a linker. The linker may be any suitable domain (i) capable to bind the biological units to the entity, and (ii) capable of releasing the one or more members of a subgroup of biological units with a physical pulse. The selection of the linker will depend on (i) the type of biological units, (ii) the entity, and (iii) the physical pulse used for releasing the one or more members of a subgroup of biological units. The skilled person will know different schemes for linking chemical compounds, nucleic acids, proteins, cells, organelles or other biological units to an entity. The linker may be bound covalently or non-covalently to the entity. Linking to the surface of the entity may be accomplished as disclosed herein. The linkers used to bind the biological units may be structurally identical or different. In one specific embodiment, the linkers are identical.

The linkers may be defined according to the physical pulse used to release the one or more members of a sub-group of the biological units. The linkers may comprise (i) A photonic cleavable part for release by a physical pulse which is generated from a light source;

(ii) A thermally cleavable part for release by a physical pulse Which is generated from a heat source;

(iii) A part of the linker which is activatable by charge, and a light sensitive reagent which, when activated by light, generates a charge that then activates the linker. In this embodiment, the detachment triggered by the light pulse does not occur before the reagent is added.

In one embodiment, the linker comprises a part a and a part b, wherein part a binds part b during binding of the group of biological units to the entity, and part a is dissociated from part b when the localized physical pulse is applied. Thus, part a and part b are binding partners which are comprised in the linker molecule. Depending on the nature of part a and part b and their mechanism of binding, part a is dissociated from part b by a specific type of physical pulse. In one embodiment, part a is dissociated from part b by heat which is produced by the physical pulse. In one embodiment, part a is dissociated from part b at a temperature of up to 50° C. at the location of the bound member. The advantage of this embodiment is that the members of the biological units which are released are not damaged. This is especially the case if the biological units are live cells. In one embodiment, said part a is dissociated from part b by photonic induced conformational changes.

In one embodiment, the one or more members which are released are harvested after release. The harvested one or more members can then be subjected to specific treatments or to analysis. After harvesting the one or more members released from the entity, further one or more members are released from the entity. The further one or more members may belong to the same sub-group, or they may belong to a different sub-group of the biological units bound to the entity via a linker.

In one embodiment, the group of biological units is a heterogeneous group of cells comprising a sub-group of cells. One or more members of the cells differ from another one or more members of the cells in at least one feature. Thus, one sub-group of cells also differs from another sub-group of cells in at least one feature. In one embodiment, a sub-group of cells comprises one or more members, wherein the one or more members are rare cells. Rare cells are cells which occur at a low frequency within a heterogeneous group of cells. The ratio of rare cells within the heterogeneous group of cells is at most 5%. In one specific embodiment, the ratio is 1%. In a further specific embodiment, the ratio is at most 0.1%. In a further specific embodiment, the ratio is at most 0.01%. The method is particularly useful for identifying and harvesting rare cells as the method allows identification of individual cells and release of these individual cells from the heterogeneous group of cells, followed by harvesting and further analysis. Rare cells may be cancer cells. In one embodiment, rare cells may be circulating tumor cells. In another embodiment, rare cells may be circulating tumor microemboli in a patient's blood. By identifying rare tumor cells using the present method, it is possible to detect a tumor long before the tumor itself is detectable by standard means, and a patient can be treated at a very early stage, thus improving survival. In addition, by using this method, the progress of a therapy can also be monitored. Furthermore, the type of tumor cell may be analyzed.

In one embodiment, in the group of cells, the ratio of a homogenous sub-group of cells to total cells is at most 50%, especially in the range of 5 to 50%, particularly in the range of 10% to 30%. This method may be used to detect a larger subpopulation of cells, e.g. cells of a particular type such as particular blood cells.

In one embodiment of the method, the sub-group of cells is indicative of a disease. In one embodiment, the disease is cancer. In one embodiment, the sub-group is composed of cells of one type.

Cancer cells are characterized by particular markers, Examples which may be mentioned are: especially oncogenes and tumor suppressor genes such as p53, genes of the ras family erb-B2, c-myc, mdm2, c-fos, DPC4, FAP, nm23, RET, WT1 and the like, LOHs, for example with regard to p53, DCC, APC, Rb and the like and also BRCA1 and BRCA2 hereditary tumors, microsatellite instability of MSH2, MLH1, WT1 and the like; also tumorous RNAs such as CEA, cytokeratins, e.g. CK20, BCL-2, MUC1, in particular tumor-specific splice variants hereof, MAGE3, Muc18, tyrosinase, PSA, PSM, BA46, Mage-1 and the like, or else morphogenic RNAs such as maspin, hCG, GIP, motilin, hTG, SCCA-1, AR, ER, PR, various hormones and the like; furthermore, especially RNAs and proteins which affect the metastasizing profile, i.e. the expression molecules involved in angiogenesis, motility, adhesion and matrix degradation such as bFGF, bFGF-R, VEGF, VEGF-Rs, such as VEGF-R1 or VEGF-R2, E-cadherin, integrins, selectins, MMPs, TIMPs, SF, SF-R and the like, the cell cycle profile or proliferation profile such as cyclins (e.g. expression ratio of cyclins D, E and B), Ki67, p120, p21, PCNA and the like, or the apoptosis profile, such as FAS (L+R), TNF (L+R), perforin, granzyme B, BAX, bcl-2, caspase 3 and the like.

Alternative diseases may also be targeted.

Alternatively, the sub-population of cells is composed of one cell type. The cells may e.g. be cardiovascular cells or vascular cells or vascular cells released by an inflammatory process or a fetal cell, e.g. a fetal cell in maternal blood, stem cells (e.g. cancerous stem cells), cells indicative of a minimal residual disease, cancer cells (e.g. leukemia cells), white blood cells. In this context, the method may be used for genotyping, diagnosis, prognosis, monitoring treatment etc.

In one embodiment of the present method, the linker is comprised of oligonucleotides, wherein part a is a first oligonucleotide and part b is a second oligonucleotide which is in part complementary to the sequence of the first oligonucleotide.

In one embodiment, part b of the linker comprises a tag b, wherein said entity is coated with a binding partner (bpb) for said tag b. Thus, part b of the linker can be bound to the binding partner bpb on the entity to immobilize the linker and the biological units. In one embodiment, the tag b is biotin, the binding partner bpb is avidin. Further binding partner pairs that may be used to bind part b of the linker to the entity are well known to the skilled person.

In one embodiment of said linker, the linker comprises a cell binding portion capable of binding the members of the sub-group. This cell binding portion should bind non-specifically to the members. This ensures that there is no selection of specific sub-groups of biological units. The cell binding portion dissociates from part b when part a dissociates from part b. Thus, the cell binding portion is associated with part a of the linker. In one embodiment, the cell binding portion of the linker is covalently associated with part a of the linker. An example of such an embodiment is shown in FIG. 2b). In another embodiment, the cell binding portion is associated with part a by non-covalent binding. In one specific embodiment, the cell binding portion comprises a tag c, and part a comprises a tag a. In this embodiment, tag c and tag a are capable of non-competitive binding of a binding partner bpa. An example of such an embodiment is shown in FIG. 2a). bpa and bpb may be the same type of binding partner. However, in one embodiment, the tag of part a and c is different from the tag of part b. The binding partner bpa for the tag of part a and part c, in this embodiment, is different from the binding partner bpb of the tag of part b.

In one further embodiment, the linker comprises a cell linker which comprises a tag that is capable of binding to the binding partner of part a in a non-competitive manner. The cell linker further comprises a biological unit binding part which is capable of binding the biological units.

Thus, in one specific embodiment, the linker is designed as shown in FIG. 3.

The dissociable parts of the linker are parts a and parts b, as described herein.

A number of affinity tags that may be used as tags in the linker are known at present. These are usually divided into 3 classes according to their size: small tags have a maximum of 12 amino acids, medium sized ones have a maximum of 60 and large ones have more than 60. The small tags include the Arg-tag, the His-tag, the Strep-tag, the FLAG-tag, the T7-tag, the V5-peptide tag, the c-Myc-tag, the medium sized ones include the S-tag, the HAT-tag, the calmodulin-binding peptide, the chitin-binding peptide and some cellulose-binding domains. The latter can contain up to 189 amino acids and are then regarded, like the GST- and MBP-tag, as large affinity tags.

Possible tag and binding partner pairs include but are not limited to biotin-avidin or streptavidin. Further exemplary pairs of tags and tag binding partners include:
6×His/Hexa-His antibody
5×His/Penta-His antibody
RGSHHHH (SEQ ID NO: 1)/RHS-His Antibody
4×His/Tetra-His Antibody
GST-tag/GST-tag antibody
Strep tag/Streptavidin
Biotin/Streptavidin
GST-tag/GST antibody
A Flag-tag (e.g. DYKDHK (SEQ ID NO: 2) or DYKDDD (SEQ ID NO: 3))/Flag-tag antibody Furthermore, a hapten and the respective antibody may be used. A hapten is a small molecule with high immunogenicity used in many molecular biology applications. Popular haptens include digoxigeninDNP (dinitrophenol), biotin, and fluorescein.

The present disclosure further relates to a method of detecting a subject's disease by isolating and analyzing a sub-group of biological units obtained from said subject. The method comprises providing a heterogeneous group of biological units comprising at least one sub-group of biological units, the group of biological units being obtained from a subject, and each member of the group of biological units being bound to an entity, preferably a solid support, via a linker. Furthermore, the method comprises determining the location of the sub-group of biological units. Once the location is determined, the method comprises applying a localized physical pulse to said one or more members, wherein said localized physical pulse individually releases said one or more members from said entity by dissociating said linker. The one or more members of the sub-group of biological units which is/are released from the entity is harvested, thereby isolating said one or more members of the sub-group of biological units. The harvested one or more members of the sub-group of biological units is analyzed for at least one marker indicative of the disease. Examples for such Markers are described herein.

In one specific embodiment, the disease is cancer. However, the disease may also be another disease that is characterized by the presence of rare cells at least in the early stages of the disease.

The group of biological units may be obtained from the subject in various ways. They may be obtained in the form of a sample. "Sample" means a quantity of material that is suspected of containing sub-groups of biological units. As used herein, the term includes a specimen (e.g. a biopsy or medical specimen) or a culture (e.g. microbiological culture). Samples may be fluid, solid (e.g. stool) or tissue. Samples may include materials taken from a patient including, but not limited to, cultures, blood, saliva, cerebral spinal fluid, pleural fluid, milk, lymph, sputum, semen, needle aspirates, and the like. In regard to a human sample or tissue sample or patient sample or patient cell or tissue sample or specimen, each means a collection of similar or biological or biochemical compounds obtained from a tissue of a subject or patient. The source of the tissue sample may be solid tissue as well as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. The tissue sample may contain compounds which are not naturally intermixed with the tissue in nature such as preservatives, anticoagulants, buffers, fixatives, nutrients, antibiotics, or the like. The biological unit may be for example a cell or a part thereof, a cellular component such as a specific protein, nucleic acid, receptor, marker, metabolite, etc., a part of a tissue or organ and the like.

The samples may be obtained e.g. by withdrawing a body fluid sample from the subject. Plasma may be prepared from blood. Leukocytes or other cellular blood components, such as lymphocytes, may be isolated from blood which was withdrawn from a subject.

The above method relates to a method of detecting a subject's disease by detecting a sub-group of biological units indicative of the disease. It is generally known that biological units of a body are indicative of diseases of that body. A multitude of examples is given herein. Accordingly, the detection of these units (e.g. specific cells, protein, nucleic acids, small molecule compounds etc.) is indicative of the disease.

The subject may be a mammal, more specifically a human or an animal.

The sub-group of biological units dissociated from the solid support to which the biological units are bound via a linker and harvested after dissociation may be further processed to determine if it is indicative of the disease. In one embodiment, a sub-component of the biological unit may be isolated. As an example, if the biological units are cells, a component of the sub-group of cells such as nucleic acids or proteins or hormone or other molecule may be further analyzed by methods well known to the skilled person such as immunoassays, PCR or other amplification method such as TMA, LCR, NASBA etc., mass spectrometry etc. in order to determine if they are indicative of the disease.

In one embodiment, the one or more members of the sub-group of biological units harvested and, thereby isolated are analyzed for at least one marker which is indicative of the disease. Such markers may be nucleic acids known to be up-regulated or down-regulated in the disease, or they may be proteins or other components comprised in the one or more members of the sub-group of biological units.

In a further embodiment, a method of isolating one or more members of a subgroup of biological units from a group of biological units is provided. The method comprises providing a heterogeneous group of biological units comprising at least one sub-group of biological units, each member of the group of the biological units being bound to an entity, preferably a solid support, via a linker. It further comprises determining the location of said one or more members of the sub-group of biological units. Following the determination of the location, it comprises applying a localized physical pulse to said one or more members, wherein said localized physical pulse individually releases said one or more members from said entity by dissociating said linker, followed by isolating the released one or more members of the subgroup of biological units.

Further specific embodiments of the method are as defined herein.

The term "isolating" as used herein means that the isolated one or more members are thereby separated from the remaining cells. In specific embodiments, the method of isolating a sub-group of objects from a group of objects is further defined as described above in the context of the method of specifically releasing a sub-group of objects from a solid support according to the present disclosure. Additional isolation steps as known to the skilled person may be added.

A device in which the methods herein described may be performed is also disclosed. Such a device comprises a shallow cavity with a width and a length, created by at least one transparent plate. In one embodiment, the plate is a glass plate. The depth of the cavity of the device may be fixed or it may be adjusted by a movable cover. In one embodiment, the size of the transparent plate is selected depending on the required surface. In another embodiment, the size is a standardized footprint, such as the footprint of a standard microscope slide or of an SBS-standard multiwell plate. The depth of the cavity can range from a few ten micrometers to a few millimeters. In one embodiment, the depth is between 10 um and 1 mm. In a more specific embodiment, the depth is between 50 um and 1 mm. In a further specific embodiment, the depth is between more than 50 um and less than 1 mm. In a more specific embodiment, the depth is around 100 um. The advantage of this depth is that cell binding to the linker is optimized, together with optimized cell distribution homogeneity and optimized sedimentation times and optimized consumed volumes. This is particularly useful for optimizing the volume of reagents necessary for staining to identify the cells. In one embodiment, the depth is adjustable. This has the advantage that it can be selected based on the specific application.

The device further includes, in one embodiment, one or more channels over the width of the plate at the entry and outlet. These channels allow for a uniform flow profile and filling of the cavity without enclosing air-bubbles. The uniform flow profile enhances staining and washing of the cells.

The cavity, transparent plate and channel may be enclosed in a module with side walls and upper and lower walls with two or more fluid ports present, at least one at each side of the cavity channel for addition of liquids, staining fluids, reagents and emulsions or cell suspensions into the channel, through the cavity along the surface and out of the module. Different formats of these ports may be chosen such as open ports, septa through which the fluids can be pipetted with a needle or connecting tubing. For filling centrifugation, pipetting or a pump can be used. For centrifugation, the inlet connection port needs to have a sufficient volume to contain the pipetted volume before the centrifugation process is started. The optically transparent plate is accessible by an optical scanner or a microscope objective for identification of sub-groups of biological units.

In another embodiment, the cover of the chamber can be removed for mechanical access.

The following non-limiting examples illustrate certain embodiments of the present subject matter.

DETAILED DESCRIPTION OF THE FIGURES

FIG. 1 shows a schematic view of a cell (1) bound to an entity (2) via linkers (3).

Figure 2:
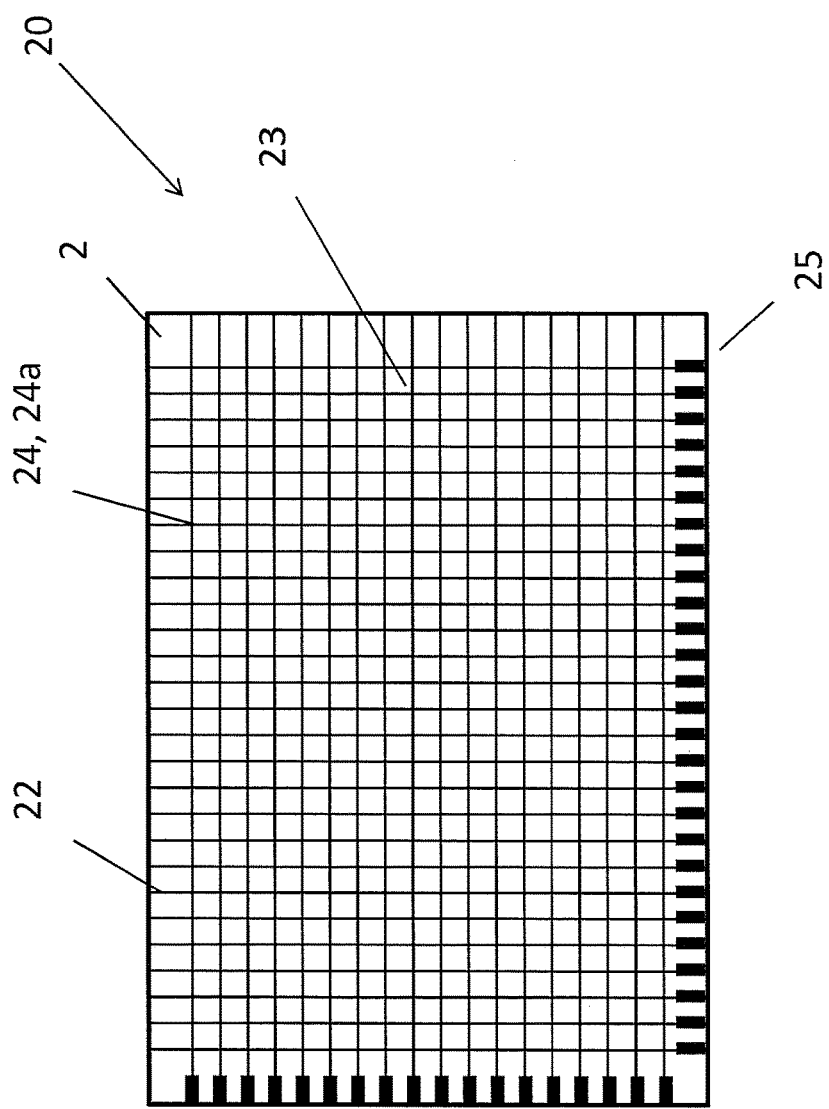
FIG. 2 shows a schematic view of an array (20) of arrangements (24, 24a) for exerting a physical localized pulse on cells attached to a substrate (2).

FIG. 2 shows an array (20) of arrangements (24, 24a) for exerting a physical localized pulse on cells attached to a substrate (2). The array (20) may comprise conductive lines (22) and crossings (23) with resistive heating elements (24) for a temperature pulse, or light elements (24a) located at each crossing (23) for optical pulses. The contact pads (25) are connected to a user or computer controlled power source in order to apply the required electrical power.

FIGS. 3a) and b) show two different embodiments of the linker (3) which is bound to cell (1) and entity (2). The linker (3) in FIG. 3a) comprises part b (8) with tag b (9). Tag b (9) is associated with binding partner bpb (10). Binding partner bpb (10) is attached to entity (2). Linker (3) further comprises part a (7) which associates with part b (8). Part a (7) comprises a tag a (12). Tag a (12) is bound to binding partner bpa (14). Cell binding portion (11), which is bound to cell (1), comprises a tag c (13). Tag c (13) is also bound to binding partner a (14). FIG. 3b) shows another embodiment of linker (3). Part b (3) comprises tag b (9) which is bound to binding partner bpb (10). Binding partner bpb (10) is bound to the entity (2). Part b (8) is associated with part a (7). Part a (7) comprises a cell binding portion (11) which is bound to cell (1).

FIG. 4 shows the process of dissociation of part a and part b for the exemplary embodiment shown in FIG. 3a). The same principle applies to the exemplary embodiment of FIG. 3b).

FIG. 4a) shows the same linker (3) of FIG. 3a) bound to cell (1) and entity Heat (15) is applied to the parts a (7) and b (8). This results in the dissociation of part a (7) and part b (8) of the linker (3) shown in FIG. 4b). As a consequence, cell (1a) is released from entity (2).

In FIG. 5, part a (7) and part b (3) are dissociated by a light pulse (36) from a light source (16), resulting in detachment of cell (1a).

FIG. 6 shows a schematic of the individual detachment of cells (1) by a physical pulse (36). a) A physical pulse (36) is exerted onto a cell (1) using a focused light source (16). b) A cell (1a) is selectively and individually released and can then be harvested by a flow (17) of liquid (18).

FIG. 7 shows an embodiment in which, following a light pulse (36) the selectively released or detached cell (1a) is removed using a pipetting instrument (19) (FIG. 7a)), which allows dispensing the aspirated liquid (18a) comprising detached cell (1a) to be dispensed onto a new surface or a receptacle (2a) (FIG. 7b)). The detached cell (1a) can then be further analysed, e.g. by determining if at least one marker specific for the disease to be tested is present in the detached cell (1a).

FIG. 8a) shows an embodiment in which a magnetic particle (26) is associated with part a (7) and is detached along with detached cell (1a). Released or detached cell (1a) can then be harvested using a magnet (27) (FIG. 8b)).

Figure 9:
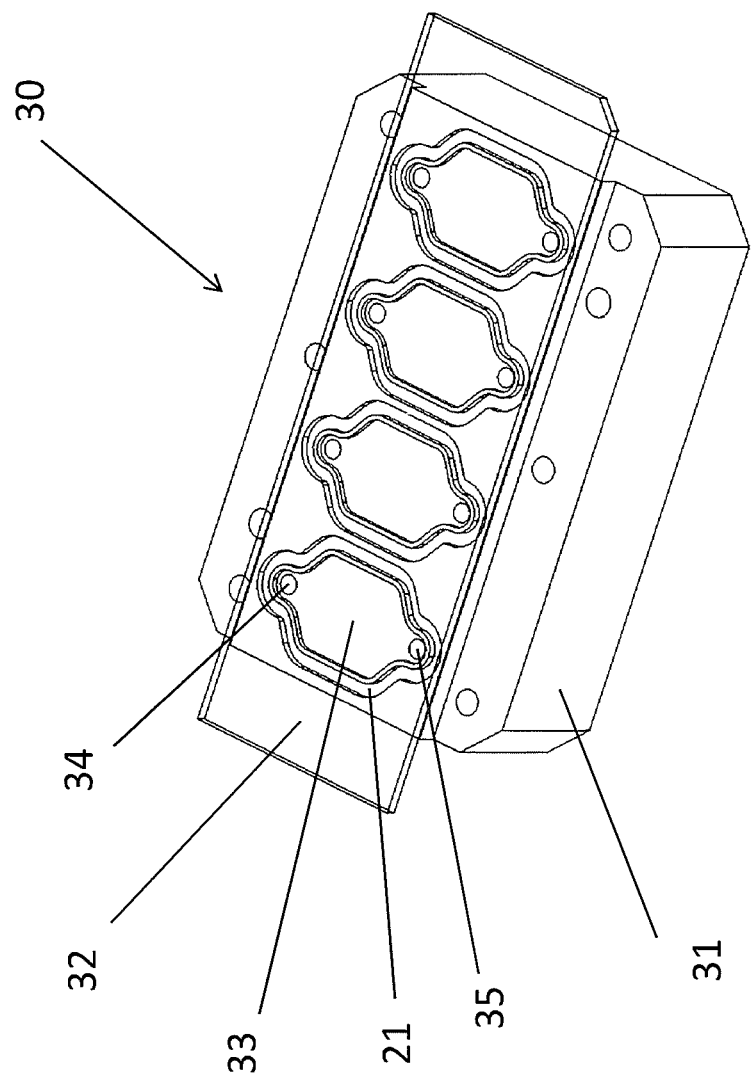
FIG. 9 shows a perspective view of an embodiment of a flow-through chamber (30) comprising a socket (31), a microscope slide (32) and compartments (33) for taking up liquid (18), an Inlet (34) for adding liquid (18) to a compartment (33) and an outlet (35) for removing liquid (18) from the compartment (33).

FIG. 9 is an embodiment of a flow-through chamber (30) comprising a socket (31), a microscope slide (32) and compartments (33) for taking up liquid (18), an Inlet (34) for adding liquid (18) to a compartment (33) and an outlet (35) for removing liquid (18) from the compartment (33). Each compartment (33) is surrounded by a seal (21) to ensure that liquid (18) can only flow through inlet (34) and outlet (35).

Figure 10:
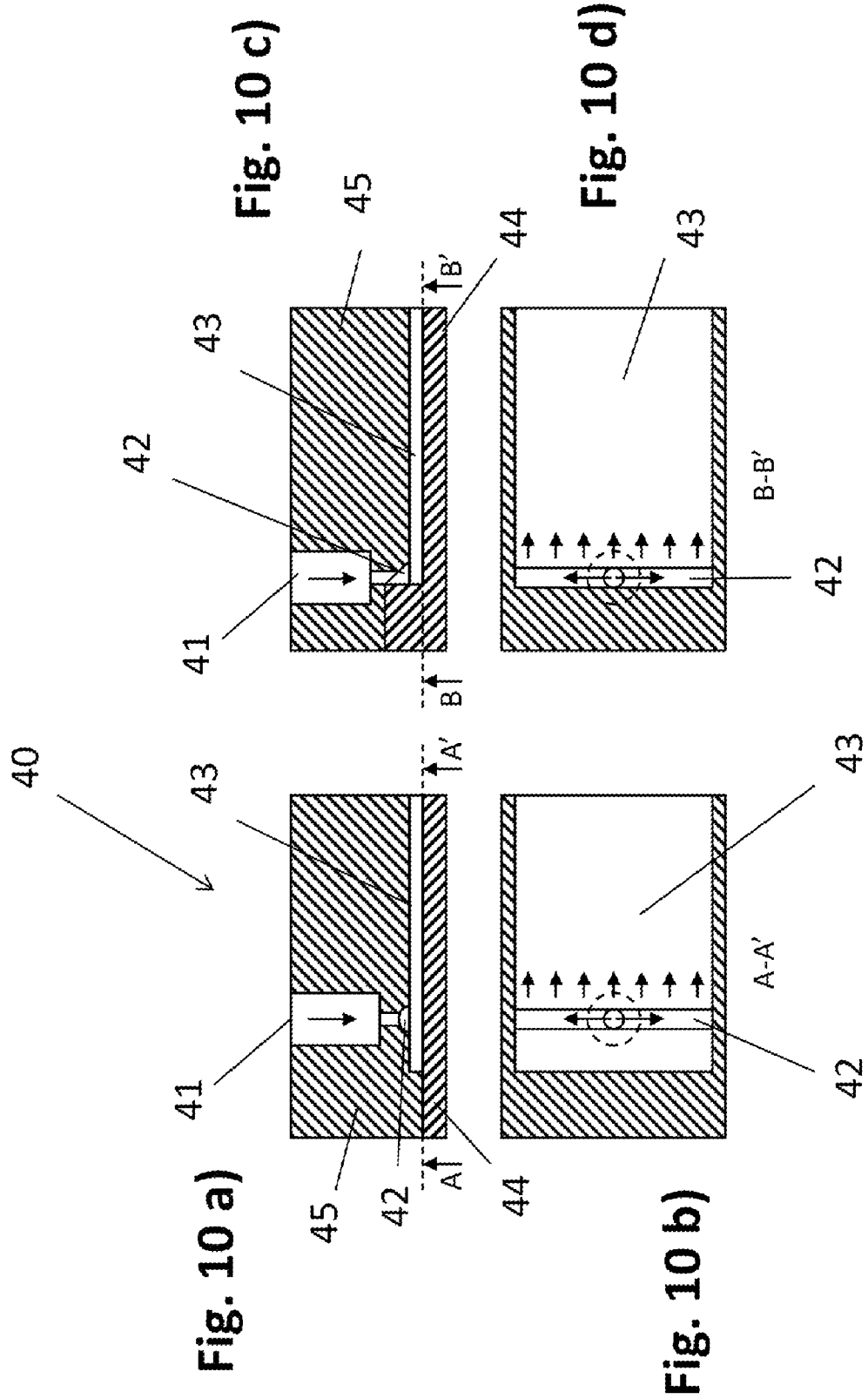
FIG. 10a) shows a schematic view of an embodiment of a centrifugation chamber (40), FIG. 10b) shows a cross-sectional view taken along a line A-A' in FIG. 10a), FIG. 10c) shows a schematic view of another embodiment of a centrifugation chamber, and FIG. 10d) shows a cross-sectional view taken along a line B-B' in FIG. 10c).

FIG. 10 is an embodiment of a centrifugation chamber (40). The centrifugation chamber (40) is suitable for immobilizing biological units (1) on an entity (2). The entity (2) may comprise linkers (3) to which the biological units (1) attach, as is shown in FIG. 1. The chamber (40) comprises a fluid inlet port (41). Liquid (18) can be added to the chamber (40) via fluid inlet port (41). The chamber (40)

further comprises a channel for uniform flow distribution (42). Liquid (18) flows from the fluid inlet port (41) through the channel for uniform flow distribution (42). The chamber (40) comprises a main chamber (43). The biological units (1) such as cells (1) can be added to the main chamber (43) by allowing liquid (18) comprising the cells (1) to the fluid inlet port (41) and allowing it to flow through the channel for uniform flow distribution (42) to the main chamber (43). The chamber (43) further comprises a lower transparent plate (44) which serves as a base and an upper mount (45) which forms the main body. The advantage of this design is that the liquid (18) comprising cells (1) can flow evenly into the main chamber (43). The lower transparent plate (44) may serve as a substrate (2) for immobilizing the cells (1). In one specific embodiment, the depth of main chamber (43) ranges from 10 micrometers to 5 millimeters. In a more specific embodiment, the depth of the main chamber (43) is between 50 micrometers and 150 micrometers. A most specific embodiment of the depth of the main chamber (43) is 100 micrometer. By this, the cell distribution is optimal. The disclosed chamber has the advantage that a reproducible, completely uniform filling without air bubbles is ensured.

Figure 11:
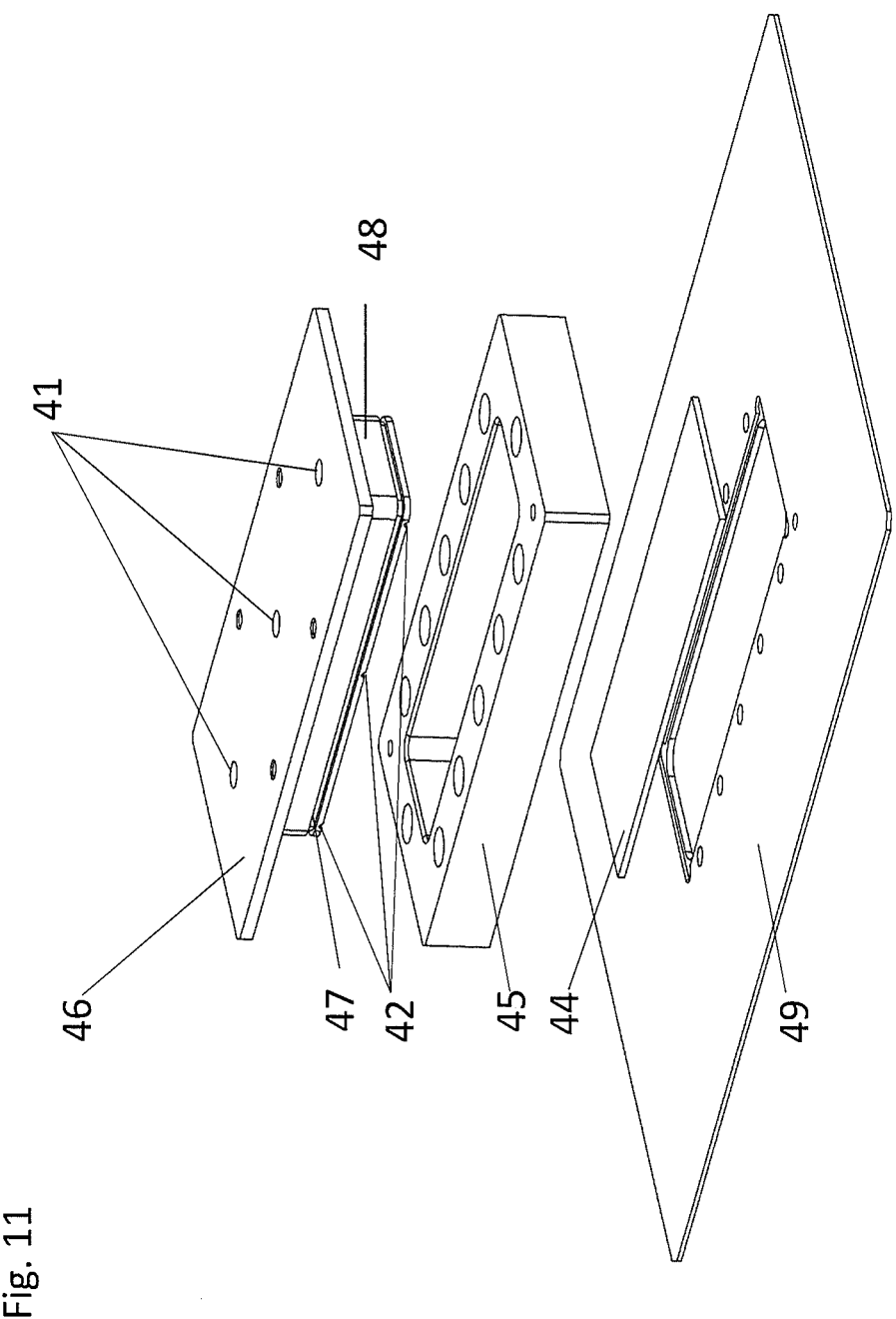
FIG. 11 shows an exploded view of the chamber (40).

FIG. 11 shows an exploded view of the chamber (40). The fluid inlet port (41) can also serve as outlet port. The chamber (40) comprises a height adjustable cover (46). The inlet ports (41) are formed in this height adjustable cover (46). An insert (48) is mounted on the cover (46). The insert (48) comprises a cover seal (47) and the channels for uniform flow distribution (42) are formed in the bottom of the insert (48). When assembled, the insert (48) is fitted into the mount forming the main channel walls (45). The lower wall of the main chamber (43) (not shown) is formed by the base plate (44). The assembly is mounted on base (49).

Following immobilization of the cells (1) on the base plate (44), the chamber (40) can be removed, and the immobilized cells can be individually released by a selective physical pulse or other appropriate method as described herein.

Centrifugation can be used to fill the chamber. It can also be used to promote binding of cells, with or without linker chemistry, to the surface, speed up sedimentation time and can be used to promote releasing and transporting the selected, detached cells. In one embodiment of the method herein described, the binding of said group of biological units comprising said sub-group of biological units to said entity via a linker is promoted by centrifugation. In one specific embodiment, centrifugation is performed in a chamber as described herein. In one embodiment, the harvesting of the detached biological unit or units is promoted by centrifugation in a chamber as described herein.

EXAMPLES

Example I

Thermally Cleavable Molecules

The experimental examples show the feasibility of the method using thermally cleavable molecules. For the purposes of easy analysis of feasibility, the used linker molecules include dyes. The dyes are not necessary for the method.

The dissociation in this example is based on denaturation of two hybridized oligonucleotides comprised in the linker. The denaturation temperature depends on the design of the oligo-nucleotides and should be above ambient temperature to ensure stable binding and below a temperature at which cells could be damaged or particles dissociated. In one specific embodiment, the denaturation temperature of the oligonucleotides of the linker is between 35° C. and 50° C. For some applications, it can be advantageous if the oligo-nucleotides are not self-hybridizing.

If using an IR light source to generate the heat pulse, the wavelength should be suitable to heat up the liquid by a high absorption coefficient. In case of an aqueous solution, light sources above 800 nm should be used. In one specific embodiment, the wavelength is near local absorption maxima (e.g. 1470 mm, 1550 nm, 1900 nm, 2870 nm).

Linker molecules used in this example are two oligo-nucleotides which can hybridize to each other. Molecule S11 is labeled with a green fluorescent dye and has the sequence 5'(CY3)-TTT-GCGAAGCGAAGCGTTTTTTTT-3'-(TEG-Biotin) (SEQ ID NO: 4). Molecule S12 is labeled with a red fluorescent dye and has the sequence 5'(ATTO647N)-TTT-CGCTTCGCTTCGCTTTTTTTT-3'(TEG-Biotin) (SEQ ID NO: 5). The entity is an avidin-coated glass slide (ArrayIt Corp, Sunnyvale, USA). A flow chamber is attached on the glass slide for functionalization and incubation. A Fluorescence scanner is used for slide imaging.

Example I (a)

Stability of Bonds Between Molecules and Entity

The stability of the bonds formed between Molecule S11 and the avidin-coated glass slide, and Molecule S12 and the avidin-coated glass slide was tested.

Molecule S12 was incubated on an avidin-coated glass slide in 10 uM PBS, 0.05% Tween-20 and 1 M NaCl at 42° C. for 60 minutes. The avidin-coated glass slide with the bound Molecule S12 was washed by flushing with PBS, 0.05% Tween-20. Red fluorescence was measured. To test the stability of the binding, the avidin-coated glass slide with the bound Molecule S12 was warmed by washing with PBS at a temperature of 55° C., followed by detection of the red fluorescent dye. No reduction of fluorescence was determined indicating that the warming and washing did not remove the linker due to stable binding between linker and avidin-coated glass surface.

Molecule S11 was incubated on an avidin-coated glass slide in 10 uM PBS, 0.05% Tween-20 and 1 M NaCl at 42° C. for 60 minutes. The avidin-coated glass slide with the bound Molecule S11 was washed by flushing with PBS, 0.05% Tween-20. Green fluorescence was measured. To test the stability of the binding, the avidin-coated glass slide with the bound Molecule 11 was warmed by washing with PBS at a temperature of 55° C., followed by detection of the green fluorescent dye. No reduction of fluorescence was determined indicating that the warming and washing did not remove the linker due to stable binding between linker and avidin-coated glass surface.

Example I (b)

Thermal Removal of Molecules

Molecule S12 was incubated on an avidin-coated glass slide in 10 uM PBS, 0.05% Tween-20 and 1 M NaCl at 42°

C. for 60 minutes. The avidin-coated glass slide with the bound Molecule S12 was washed by flushing with PBS, 0.05% Tween-20.

Molecule S11 was incubated with the avidin-coated glass slide with the bound Molecule S12 in 10 uM PBS, 0.05% Tween-20 and 1 M NaCl at 42° C. for 60 minutes. The avidin-coated glass surface with the hybridized Molecule S12 and S11 was washed by flushing with PBS, 0.05% Tween-20. Both red and green fluorescence were measured at this point. The removal of detachment of Molecule S11 was then tested by warming the glass slide with the linker by flushing with PBS, 0.05% Tween-20. Red and green fluorescence were measured again. 65% to 70% of Molecule S11 was removed from the glass slide while no removal of Molecule S12 could be detected.

Example II

Removal of Fluorescent Heads Without Spatial Resolution

Linkers and entity were as described in Example 1. Fluorescent beads were obtained from Spherotech Inc., lake Forest, USA (TFP 7052-5). They had a diameter of 7 to 8 micrometers and were coated with biotin and a fluorescent yellow dye. A flow chamber as shown in FIG. 9 was used, together with an optical fluorescence microscope and resistive heating with uniform slide heating, i.e. the complete slide was heated uniformly.

Molecule S12 was immobilized on the glass slide as described in Example 1. Biotin was added for saturation of the binding sites on the avidin-coated glass slide by incubation in 10 uM PBS, 0.05% Tween-20 and 1 M NaCl at 42° C. for 60 minutes, followed by flushing with PBS, 0.05% Tween-20. Molecule S11 was incubated with the avidin-coated glass slide with the bound Molecule S12 in 10 uM PBS, 0.05% Tween-20 and 1 M NaCl at 42° C. for 30 minutes. This was followed by incubation at room temperature for 30 minutes and subsequent flushing with PBS, 0.05% Tween-20. Avidin was bound to the biotin coupled to Molecule S11 by incubation in 10 uM PBS, 0.05% Tween-20 at room temperature for 30 Minutes, followed by flushing with PBS, 0.05% Tween-20. Then, the biotin coated fluorescent beads were bound to the avidin undiluted, at 0.1 w/v % by incubation at room temperature in the dark for 30 minutes, followed by flushing with PBS, 0.05% Tween-20.

Imaging was performed before and after flushing with 50 mm/s and no heating. No removal could be detected. The number of beads bound to the glass slide remained constant (+/−6%).

Imaging was also performed before and after flushing while heating the liquid in the chamber up to 60° C. and 70° C. The removal rate of fluorescent beads was 40 to 60%, with the remaining beads being uniformly distributed. Beads directly bonded to the glass surface without linking molecule remained on the surface at a flushing speed of 100 mm/s and heating to more than 60° C.

The heating temperature is the temperature in proximity of the heat source. The temperature in proximity of the biological unit is expected to be lower.

Example III

Removal of Fluorescent Beads with Spatial Resolution

Linker molecules S11 and S12, entity were as described in Example 1. Fluorescent beads were as in Example 2. The setup comprised a flow chamber and optical fluorescence microscope as in Example 2. However, localized resistive heating elements such as shown in FIG. 2 were arranged in the flow chamber for a localized heat pulse exerted on the slide. In this experiment, we used single heating junctions instead of an array of heating elements.

The process of coating and hybridizing and binding was as described in Example 2.

Imaging was performed before and after flushing with 50 mm/s and no heating. No removal could be detected. The number of beads bound to the glass slide remained constant (+/−6%).

Imaging was performed before and after flushing with 100 mm/s and a local heating pulse of up to 1.5 W for 30 seconds. Beads in proximity of the heat source were completely flushed away while beads located further away from the heat source remained bound. All beads within a perimeter of the heat source were removed. Beads directly bonded to the glass surface without linking molecule remained on the surface at a flushing speed of 100 mm/s and heating up to 1.5 W for 60 seconds.

Example IV

Photonic Cleavable Linker Molecules

Instead of using a linker with a part a and a part b which can be dissociated by a heat pulse, part a and part b may be a molecule which can be cleaved by photons. The appropriate light source for cleaving such a linker depends on the design of the linker. The dissociation wavelength ranges from visible below 450 nm to UV below 200 nm. Specific ranges are 280 to 350 nm and/or 360 to 450 nm. The removal of the biological unit bound to the entity via the linker is triggered by a light pulse which leaves the linker molecule. One example of such a photocleavable linker is shown in Bioconjugate Chem., Vol 15, No. 5, 2004, page 1033, Scheme 2: Photolysis of SSTN. In this example, a UV light pulse at 297 nm cleaves the molecule SSTN. Other examples of suitable molecules which are photocleavable are disclosed in WO2011/058721.

Example V

Charge-dependent Immobilization and Combined Release with Optical Pulse and Reagent In this embodiment, the detachment process must first be enabled by a reagent and is subsequently triggered by a light pulse. The process involves, in a first step, incubation of cells with cationic linker molecules to provide charges to the cell surface. Then, the cells are immobilized on a charged surface (glass or modified glass surface). Subsequently, analysis, treatment and selection of cells occur.

For removal of individual cells, a photo acid generator is first added as enabling reagent. Then, a light pulse (UV) is applied to selected cells. By this, the photo acid generator generates charges that compensate the surface charges and thus reduces the binding forces. A localized light pulse generates a local change in ion concentration which permits a selective release of cells. The wavelength of the light source for activation of the photo-cleavable part ranges from visible below ca. 460 nm UV below 200 nm; a particular range is 230 to 460 nm.

While the foregoing embodiments have been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A method of individually releasing from an entity one or more members of a sub-group of biological units comprised in a heterogeneous group of biological units, comprising:
   (a) binding said heterogeneous group of biological units to said entity via a linker, wherein all members of said heterogeneous group are bound to said entity by identical linkers;
   (b) determining a location of each of said one or more members on said entity; and
   (c) applying a localized physical pulse to each individual member of said one or more members after the determining step (b) and thereby individually releasing said individual member from said entity by dissociating said linker between said individual member and said entity, wherein said localized physical pulse comprises a photonic light pulse, a thermal pulse, or a combination thereof.

2. The method of claim 1, wherein said determining step (b) is performed by observation with a microscope, a scanning microscope, or an optical scanner.

3. The method of claim 1, wherein said localized physical pulse is a thermal pulse and said individual member is released by heat produced by said thermal pulse.

4. The method of claim 3, wherein said individual member is released at a temperature of up to 50° C. at the location of a bound member.

5. The method of claim 1, wherein said localized physical pulse is a photonic light pulse and said individual member is released by a photonic induced conformational changes.

6. The method of claim 1, wherein said individual member is harvested after release.

7. The method of claim 6, wherein, after harvesting said individual member an additional one or more of said plurality of sub-group members are individually subjected to said applying step (c) and thereby released from said entity.

8. The method claim 1, wherein said group of biological units is a heterogeneous group of cells comprising a sub-group of cells.

9. The method of claim 8, wherein said sub-group of cells comprises one or more members, wherein said one or more members are rare cells.

10. The method of claim 8, wherein the sub-group of cells is indicative of a disease, or composed of cells of one type.

11. The method of claim 1, wherein the linker molecules are comprised of oligonucleotides including a first oligonucleotide and a second oligonucleotide which is in part complementary to the sequence of the first oligonucleotide.

12. The method of claim 1, wherein the linker comprises a tag and wherein said entity is coated with a binding partner for said tag.

13. The method according to claim 1, wherein said binding step (a) includes centrifugation to promote binding between members of said heterogeneous group and said entity.

* * * * *

SEQUENCE LISTING

```
<160> NUMBER OF SEQ ID NOS: 5

<210> SEQ ID NO 1
<211> LENGTH: 7
<212> TYPE: PRT
<213> ORGANISM: Artificial Sequence
<220> FEATURE:
<223> OTHER INFORMATION: tag sequence

<400> SEQUENCE: 1

Arg Gly Ser His His His His
1               5

<210> SEQ ID NO 2
<211> LENGTH: 6
<212> TYPE: PRT
<213> ORGANISM: Artificial Sequence
<220> FEATURE:
<223> OTHER INFORMATION: tag sequence

<400> SEQUENCE: 2

Asp Tyr Lys Asp His Lys
1               5

<210> SEQ ID NO 3
<211> LENGTH: 6
<212> TYPE: PRT
<213> ORGANISM: Artificial Sequence
<220> FEATURE:
<223> OTHER INFORMATION: tag sequence

<400> SEQUENCE: 3

Asp Tyr Lys Asp Asp Asp
1               5

<210> SEQ ID NO 4
<211> LENGTH: 24
<212> TYPE: DNA
<213> ORGANISM: Artificial Sequence
<220> FEATURE:
<223> OTHER INFORMATION: oligonucleotide

<400> SEQUENCE: 4
tttgcgaagc gaagcgtttt tttt                                          24

<210> SEQ ID NO 5
<211> LENGTH: 24
<212> TYPE: DNA
<213> ORGANISM: Artificial Sequence
<220> FEATURE:
<223> OTHER INFORMATION: oligonucleotide

<400> SEQUENCE: 5
tttcgcttcg cttcgctttt tttt                                          24
```